US010405994B2

United States Patent
Logan et al.

(10) Patent No.: US 10,405,994 B2
(45) Date of Patent: Sep. 10, 2019

(54) FEMORAL SIZER

(71) Applicant: Howmedica Osteonics Corp., Mahwah, NJ (US)

(72) Inventors: Scott G. Logan, Oak Ridge, NJ (US); Gearoid Walsh, Clare (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 299 days.

(21) Appl. No.: 15/267,476

(22) Filed: Sep. 16, 2016

(65) Prior Publication Data
US 2017/0079739 A1 Mar. 23, 2017

Related U.S. Application Data

(60) Provisional application No. 62/220,483, filed on Sep. 18, 2015.

(51) Int. Cl.
*A61F 2/46* (2006.01)
*A61B 90/00* (2016.01)
*A61B 17/15* (2006.01)

(52) U.S. Cl.
CPC .......... *A61F 2/4657* (2013.01); *A61B 17/155* (2013.01); *A61B 90/06* (2016.02); *A61B 2090/061* (2016.02)

(58) Field of Classification Search
CPC .... A61B 17/155; A61B 5/4585; A61F 2/4657
See application file for complete search history.

(56) References Cited

U.S. PATENT DOCUMENTS

| | | |
|---|---|---|
| 5,445,642 A | 8/1995 | McNulty et al. |
| 5,486,178 A | 1/1996 | Hodge |
| 5,562,675 A | 10/1996 | McNulty et al. |
| 5,569,261 A | 10/1996 | Marik et al. |
| 5,662,656 A | 9/1997 | White |
| 5,688,282 A | 11/1997 | Baron et al. |
| 5,776,137 A | 7/1998 | Katz |
| 5,810,831 A | 9/1998 | D'Antonio |
| 6,013,081 A | 1/2000 | Burkinshaw et al. |
| 6,290,704 B1 | 9/2001 | Burkinshaw et al. |
| 6,458,135 B1 | 10/2002 | Harwin et al. |
| 7,261,719 B1 | 8/2007 | Twomey et al. |
| 7,488,324 B1 | 2/2009 | Metzger et al. |
| 8,216,244 B2 | 7/2012 | Green, II et al. |
| 9,050,197 B2 * | 6/2015 | Lorio ..................... A61F 2/4657 |
| 2006/0241634 A1 | 10/2006 | Tuttle et al. |
| 2010/0305575 A1 | 12/2010 | Wilkinson et al. |
| 2010/0331848 A1 | 12/2010 | Smith et al. |
| 2012/0265496 A1 * | 10/2012 | Mahfouz ................ A61B 17/14 703/1 |
| 2012/0283738 A1 | 11/2012 | Green, II et al. |

* cited by examiner

*Primary Examiner* — Andrew Yang
(74) *Attorney, Agent, or Firm* — Lerner, David, Littenberg, Krumholz & Mentlik, LLP

(57) ABSTRACT

A surgical referencing guide includes a body having a contact surface and a first foot extending away from the body. The first foot includes a first reference surface having a first area defined by a standard deviation of a first dataset extracted from a database and being comprised of a plurality of first data points each corresponding to an individual bone within a population of bones and each corresponding to a location of a preselected point on the bone within a predetermined coordinate system.

8 Claims, 4 Drawing Sheets

FEMORAL SIZER

CROSS-REFERENCE TO RELATED APPLICATIONS

This application claims the benefit of the filing date of U.S. Provisional Patent Application No. 62/220,483, filed Sep. 18, 2015, the disclosure of which is hereby incorporated herein by reference.

BACKGROUND OF THE INVENTION

Total knee arthroplasty ("TKA") and partial knee arthroplasty ("PKA") are common procedures for treating knee pain associated with different maladies. In both TKA and PKA, the joint surfaces of the tibia and femur are resurfaced to receive joint prostheses through a series of resections that remove carefully measured portions of bone. While many different techniques may be utilized during such surgeries, instruments are often provided for ensuring the necessary resections are made to allow for the proper alignment of implanted prostheses. For instance, the distal femur may be measured utilizing various instruments in order to help determine the optimal prosthesis size for the particular patient and to help determine the amount of bone to be removed.

One such instrument is referred to as an anterior/posterior ("A/P") sizer, an example of which is shown in U.S. Pat. No. 6,013,081, and is typically utilized to measure the distance between the anterior cortex of the femur and the most prominent aspect of the posterior femoral condyle(s). Current A/P sizers have a pair of feet (or a foot when performing a PKA) that are inserted through an incision in the patient's soft tissue and placed in contact with the most prominent aspect of the posterior condyles. Ensuring contact with the posterior condylar prominences, which as used herein means the most posteriorly prominent point of the posterior condyles, is important as failure to reference these landmarks can affect the final positioning and sizing of the femoral prosthesis.

Current A/P sizers are constructed to be universal to the right and left legs of the entire population of patients. Such devices are also provided with feet that have long broad reference surfaces in order to ensure contact with the posterior condylar prominences, the precise locations of which are generally unknown, and account for variances in the locations of these prominences between each patient and each leg. However, such feet are exceedingly large and difficult, if not outright impossible, to utilize in a minimally invasive TKA or PKA. In other words, the sheer size of the feet of existing A/P sizers often require a large incision and extensive arthrotomy to allow the feet to access the posterior condyles, which may complicate patient recovery and increase recovery time.

Therefore, there exists a need for an improved femoral sizer instrument for use in TKA and/or PKA procedures.

BRIEF SUMMARY OF THE INVENTION

Accordingly, the present disclosure describes several A/P sizers with feet having reduced profiles over that of their traditional counterparts that allow for placement within a minimally invasive incision while still being capable of determining the location of the posterior condylar prominences. Such feet, as described herein, have reference surfaces being sized and located with respect to one another and with respect to a distal condyle contact surface based on a refined understanding of the location of the posterior condylar prominences determined by a statistical probability that the particular patient's posterior condylar prominences are located within a well-defined region. This region may be determined by a statistical analysis of a dataset extracted from a database containing Cartesian coordinates of the posterior condylar prominences of a diverse population of individual femur bones. Such population may be refined to coincide with the patient's specific gender, height, and/or particular leg (i.e., left or right) on which the procedure is being performed.

Additionally, the several A/P sizers disclosed herein may be utilized to set the internal/external ("I/E") rotation of the final femoral prosthesis. Traditional A/P sizers generally externally rotate the final prosthesis 3 degrees with respect to the posterior condylar axis irrespective of the population to which the patient belongs. As described herein, the presently disclosed A/P sizers may utilize a database containing a diverse population of individual femurs and tibias to more precisely set the rotational position of the final prosthesis based on the individual patient.

In one aspect of the present disclosure, a surgical referencing guide, includes a body having a contact surface, and a first foot extending away from the body and having a first reference surface. The first reference surface has a first area defined by a standard deviation of a first dataset extracted from a database and being comprised of a plurality of first data points each corresponding to an individual bone within a population of bones and each corresponding to a location of a preselected point on the bone within a predetermined coordinate system.

Additionally, the predetermined coordinate system may be a Cartesian coordinate system. The standard deviation may also be the third standard deviation of the dataset. The first area may be in the shape of an ellipse. Also, the population may be a gender specific population. The bone may be a femur bone and the population may be a gender and leg specific population. The preselected point may be the most posterior point of a medial femoral condyle of each individual.

Continuing with this aspect, the surgical referencing guide may further include a second foot coupled to and extending away from the body and having a second reference surface. The second reference surface may have a second area defined by a standard deviation of a second dataset. The second dataset may be extracted from the database and may be comprised of a plurality of second data points each corresponding to an individual bone within the population of bones and each corresponding to the location of the most posterior point of a lateral femoral condyle of each individual bone within a predetermined coordinate system.

In addition, the contact surface and first and second reference surfaces may be planar, and the first and second reference surfaces may be orthogonal to the contact surface. Also, the first and second reference surfaces may be coplanar and may define a posterior reference plane. The body may also include a first and second aperture extending therethrough. The first and second apertures may be intersected by an axis oriented at an angle with respect to the posterior reference plane. The angle may be defined by a mean angle of the population as measured between a posterior condylar axis and a transverse axis orthogonal to a tibial shaft axis of each individual within the population.

In another aspect of the present disclosure, a surgical referencing guide includes a body having a contact surface, and a first foot extending away from the body and having a first reference surface. The first reference surface has a first centroid spaced from the contact surface a first distance. The first distance is defined by a mean distance between a first dataset and a reference plane, the first dataset being extracted from a database and being comprised of a plurality of data points each corresponding to an individual bone within a population of bones and each corresponding to a location of a preselected point on the bone within a predetermined coordinate system.

Additionally, the preselected point may be the most posterior point of a medial femoral condyle of each individual, and the reference plane may be a fixed plane that lays tangent to the most distal points of a medial and lateral condyle of each individual. The surgical referencing guide may further include a second foot coupled to and extending away from the body, which may include a second reference surface. The second reference surface may have a second centroid spaced from the contact surface a second distance. The second distance may be defined by a mean distance between a second dataset and the reference plane. The second dataset may be extracted from the database and may be comprised of a plurality of data points each corresponding to the location of the most posterior point of a lateral femoral condyle of each individual. The first and second centroids may be spaced apart by a third distance defined by a mean distance between the data points of the first and second datasets.

In a further aspect of the present disclosure, a surgical referencing guide includes a body having a first surface defining a first plane and a first and second aperture extending through the first surface. The first and second apertures are intersected by an axis, and a first and second foot extends away from the body. The first foot has a first reference surface and the second foot has a second reference surface. The first and second reference surfaces are coplanar and define a second plane. The axis and second plane intersect at an angle that is defined by a mean angle of a population of individuals as measured between a posterior condylar axis and a transverse axis orthogonal to a tibial shaft axis of each individual within the population.

In addition, the first and second reference surfaces may each have an elliptical shape. The first foot may be coupled to the body by a first leg, the second foot may be coupled to the body by a second leg, and the first and second legs may be separated by a distance that tapers outwardly from the body toward the feet. The population may be gender specific.

In yet a further aspect of the present disclosure a method of manufacture of a surgical reference guide, includes the steps of forming a body having a contact surface; extracting a dataset from a database, the dataset is comprised of a plurality of data points each corresponding to an individual bone within a population of bones and each corresponding to a location of a preselected point on the bone within a predetermined coordinate system; and forming a foot having a first reference surface having an area defined by a standard deviation of the dataset, and said foot connected to the body via a leg.

In a still further aspect of the present disclosure, a method of manufacture of a reference foot of a surgical reference guide having a body and at least one leg extending from the body, includes the steps of selecting a dataset from a database, the dataset comprised of a plurality of data points each corresponding to a location of a point on an individual bone within a population of bones and within a predetermined coordinate system; determining a mean and standard deviation of the dataset; and forming a reference surface of the reference foot such that the reference surface has an area based on a standard deviation of the dataset.

In addition, determining the standard deviation may include determining the third standard deviation of the dataset. The area may include a centroid and an outer boundary. The outer boundary may be spaced from the centroid a distance substantially equal to the third standard deviation of the first dataset. The method may also include determining a line slope of the dataset, and coupling the reference foot to the at least one leg such that the reference foot has an orientation with respect to a contact surface of the body based on the line slope.

In an additional aspect of the present disclosure, a method of manufacture of a surgical reference guide includes the steps of determining a mean distance of a posterior condylar prominence from a distal condylar prominence from a population of femurs; forming a body having a planar contact surface; forming a leg extending from the body; and forming a foot extending from the leg and being spaced from the reference surface based on the mean distance.

Additionally, forming the foot may include forming a reference surface disposed on the foot having an area. The area may have a centroid spaced from the reference surface a distance substantially equal to the mean distance. The area may be defined by a standard deviation from a mean location within a preselected coordinate system of the posterior condylar prominence within the population of femurs.

BRIEF DESCRIPTION OF THE DRAWINGS

These and other features, aspects, and advantages of the present invention will become better understood with regard to the following description, appended claims, and accompanying drawings where:

DETAILED DESCRIPTION

When referring to specific directions in the following discussion of certain surgical instruments, it should be understood that such directions are described with regard to the surgical instrument's orientation and position during exemplary application to the human body. Thus, as used herein, the term "proximal" means close to the heart and the term "distal" means more distant from the heart. The term "anterior" means toward the front of the body or the face and the term "posterior" means toward the back of the body. The term "medial" means toward the midline of the body and the term "lateral" means away from the midline of the body. Also, as used herein, the terms "about," "generally" and "substantially" are intended to mean that deviations from absolute are included within the scope of the term so modified.

Figure 1A:
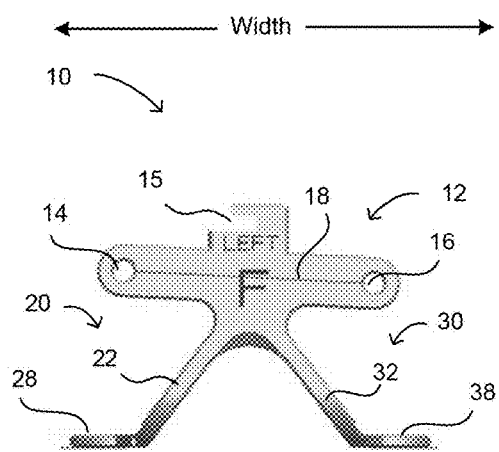
FIG. 1A is a front view of a left leg, female specific A/P sizer in accordance with the present invention.
Figure 1C:
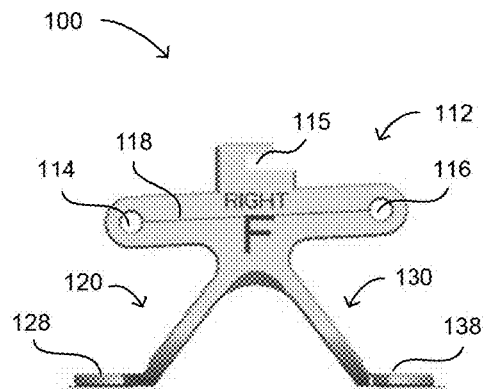
FIG. 1C is a front view of a right leg, female specific A/P sizer.
Figure 1B:
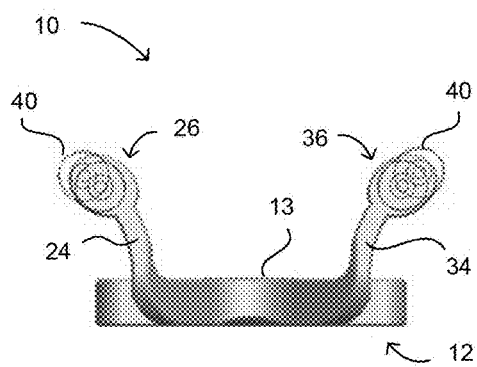
FIG. 1B is a bottom view of the A/P sizer of FIG. 1A.

FIGS. 1A and 1B depict one embodiment of a left leg, female specific A/P sizer 10 in accordance with the present invention, which may also be referred to herein as a surgical or condylar referencing guide. As will be described in more detail below, A/P sizer 10 is designed for use in a TKA procedure where the distal femur has been resected in accordance with a mechanical axis alignment technique. However, as is also described below, A/P sizer 10 may be designed for use in a TKA where the distal femur has been resected according to an anatomic axis alignment technique or where the distal femur has not been resected and referencing is based on unresected condylar surfaces.

A/P sizer 10 is particularly useful for minimally invasive TKA, but may also be utilized in standard TKA, and generally includes a body 12, a pair of legs 20, 30, and a pair of feet 26, 36. Feet 26 and 36 are coupled to body 12 via legs 20 and 30, respectively. In some embodiments, A/P sizer 10 may not include legs, but rather may include feet coupled directly to body 12 and extending therefrom. In other embodiments, particularly for use in PKA, A/P sizer 10 may only include a single leg and foot coupled to body 12, or, alternatively, a single foot coupled to body 12 or a body similar to body 12, but having a reduced size for contacting a single distal condyle rather than both condyles.

Body 12 is designed to contact and reference a distal resected surface of a femur. As shown, body 12 includes a planar reference or bone contact surface 13 for contacting and referencing the distal resected surface. Such distal resected surface may be formed by resecting a distal femur. However, it should be understood that such planar reference surface 13 can be used to reference an unresected distal femur.

Body 12 also includes first and second apertures 14, 16. First and second apertures 14, 16 extend through the entirety of body 12 (as best shown in FIG. 1A), and are each intersected by an axis 18, which in some embodiments may bisect body 12. The distance or width between apertures 14 and 16 may correspond with other instrumentation (e.g., corresponding apertures in a 4-in-1 cutting block) and/or with a femoral prosthesis (e.g., corresponding pegs extending from an inner surface of a femoral component). The lateral-medial width ("L/M width") of body 12 may be sufficiently large to provide for such apertures 14 and 16, but may preferably be no larger to keep the size of guide 10 to a minimum. Of course, some embodiments may include structure that extends beyond what is needed to provide for apertures 14 and 16, for example, for enhanced grip.

Body 12 also includes an engagement slot 15, which is configured to receive and retain an additional surgical instrument, such as a stylus, blade runner, or the like to aid in the sizing of the femoral prosthesis (discussed more fully below). Slot 15 is preferably disposed near the midline of body 12 and opens in a medial to lateral direction.

Figure 4A:
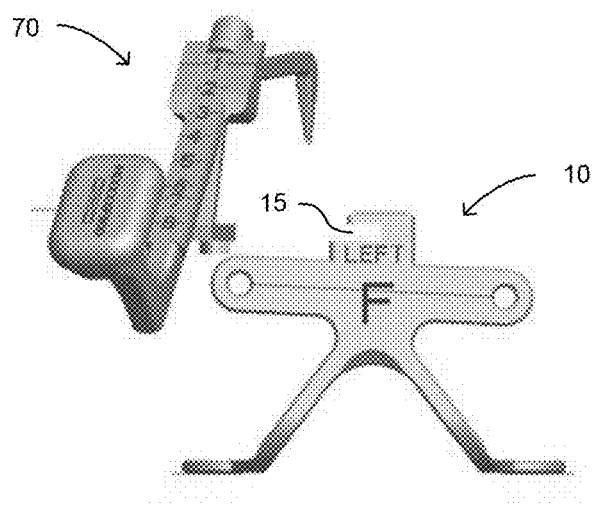
FIG. 4A is an exploded front perspective view of the A/P sizer of FIG. 1A and a stylus.
Figure 4B:
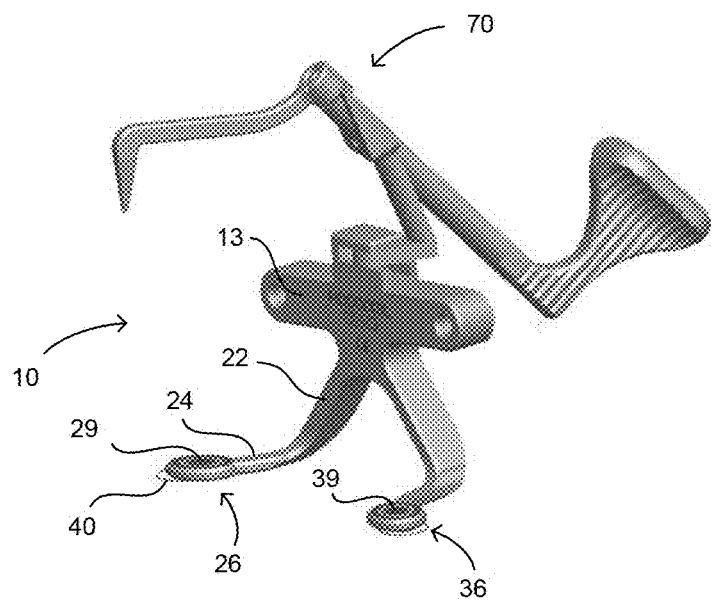
FIG. 4B is a rear perspective view of the A/P sizer and stylus of FIG. 4A assembled together.

The pair of legs more specifically includes a lateral leg 20 and a medial leg 30. Legs 20 and 30 preferably join together at body 12 and extend outwardly such that the distance separating lateral and medial legs 20, 30 is greater further from body 12. Legs 20 and 30 preferably each have a first portion 22, 32 that includes a surface coplanar with the bone contact surface of body 12, which helps prevent legs 20 and 30 from interfering with referencing a distal resected surface, and a second portion 24, 34 that curves away from a respective first portion 22, 32 and body 12 (best shown in FIG. 4B). The ends of second portions 24 and 34 bend outwardly and are each joined with a foot 26, 36. As best shown by FIG. 1B, due to the bends in each leg and the tapered distance between each leg, the L/M width of A/P sizer 10 is smaller at legs 20 and 30 than at the feet 26 and 36. This aids in the use of A/P sizer 10 during minimally invasive TKA as the smaller L/M width at legs 20 and 30 allows feet 26 and 36 to be successively passed through a minimally invasive incision, which may allow the incision itself to have a maximum L/M width smaller than the L/M width of the A/P sizer at feet 26 and 36. This varies considerably from traditional A/P sizers, which typically have a constant L/M width from the bone contact surface of the body to the end of the legs or end of the feet.

The pair of feet more specifically includes a lateral foot 26 coupled to lateral leg 20 and a medial foot 36 coupled to medial leg 30. Each foot includes a reference surface 28, 38 that is preferably planar for contacting and referencing a posterior condylar prominence. In order to maintain a low profile while ensuring that each reference surface 28, 38 will contact a posterior condylar prominence, the size, shape and location of reference surfaces 28 and 38 with respect to bone contact surface 13 are optimized based on information retrievable from a database.

As used herein, database means a collection of several datasets, a dataset means a collection of several data points, and a data point means a single measurement of a desired variable derived from an individual within a population. Such measurement can be a location of the variable within a coordinate system, such as a Cartesian or polar coordinate system. A population, as used herein, means a group of individuals each satisfying certain characteristics, such as gender, height, weight, right or left leg, femur bone, tibial bone, or the like. For example, a population of femur bones may be comprised of individual femur bones each belonging to a subject being six foot tall or taller. One example of a database is the Stryker Orthopaedics Modeling and Analytics ("SOMA") database, which catalogues various bone morphology datasets relating to size, shape, density, cortical boundaries, location of bony landmarks, and the like, drawn from a collection of individual bones, such as a femur bone and tibia bone.

Figure 2:
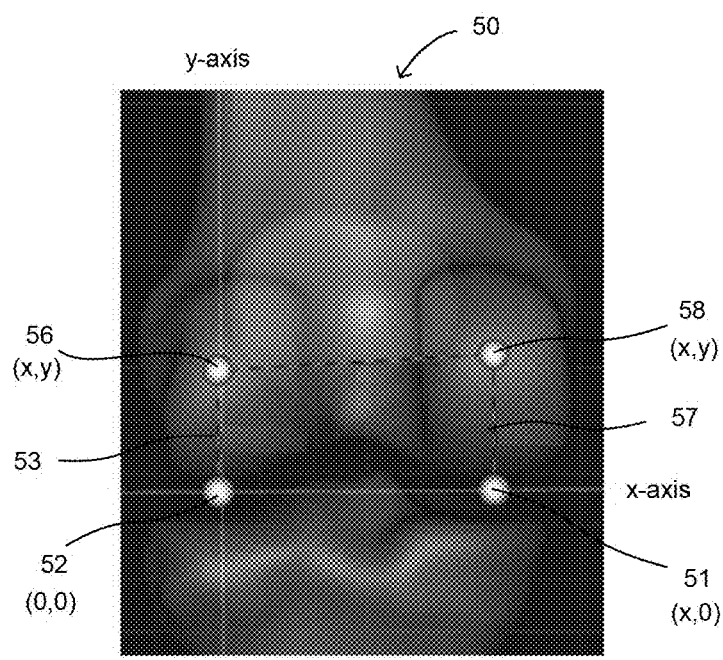
FIG. 2 is a two dimensional view of data points overlaying a schematic representation of a femur.

As illustrated in FIG. 2, in one embodiment of A/P sizer 10, the SOMA database, or the like, is utilized to extract data points relating to the location of distal condylar and posterior condylar prominences from a statistically significant population of femur bones. Such locations may be measured in a two dimensional Cartesian coordinate system where, for instance, each data point has a corresponding x and y value as measured from a fixed origin, which by way of example, may be located at data point 52, which relates to a lateral distal condylar prominence. In addition, an x-axis within the coordinate system may be oriented so that the x-axis lies tangent to data point 51, which relates to a medial distal condylar prominence.

This x-axis determined through the database can then be related to the locations of the posterior condylar prominences 56 and 58. This relationship may be utilized to configure A/P sizer 10. More particularly, the relationship of body 12 relative to feet 26 and 36 and the feet relative to each other. For example, in some embodiments sizer 10 is configured to contact unresected distal condyles of a femur. In such embodiments, the x-axis, as shown in FIG. 2, may correspond to reference surface 13 of body 12, and the posterior condylar prominences 56 and 58 may correspond to feet 26 and 36, respectively.

In other embodiments, sizer 10 may be configured to contact a distal resected surface of a femur. Such distal resected surface may be formed according to a mechanical or anatomic axis alignment technique prior to using sizer 10. Due to the distal condyles being removed by such resection, sizer 10 is configured such that feet 26 and 36 are closer to reference surface 13 than embodiments for contacting an unresected distal femur. This can be done by repositioning the origin and the x-axis to align with a location and orientation of a distal resected surface, which may be known relative to the distal condylar prominences 51 and 52. Such repositioned x-axis may extend through lines 53 and 57, which connect distal condylar prominences 51 and 52 with the posterior condylar prominences 56 and 58. Therefore, in embodiments configured for contacting a distal resected surface, feet 26 and 36 are positioned closer to body 12 than in embodiments configured for contacting an unresected distal femur.

In addition, the distances of the posterior condylar prominences 56 and 58 relative to the x-axis in embodiments of sizer 10 configured to contact a distal resected surface of a femur may vary depending on the type of alignment technique utilized to form the distal resected surface of a femur. Such alignment techniques determine an orientation of the distal resected surface. Thus, sizer 10 would be configured to account for such orientation so that feet 26 and 36 can contact the posterior condyles in a minimally invasive, low profile way. For example, in a mechanical axis alignment technique, lateral posterior condylar prominence 56 would be closer to the x-axis than the medial posterior condylar prominence 58. As such, in a sizer configured for use in a mechanical alignment, foot 26 would be closer to reference surface 13 than foot 36. Conversely, in an anatomic axis alignment technique, lateral posterior condylar prominence 56 would be further from the x-axis than the medial posterior condylar prominence 58. As such, in a sizer configured for use in an anatomic alignment, foot 26 would be further from reference surface 13 than foot 36.

Thus, the locational information of the posterior condylar prominences extracted from the database with respect to the fixed origin and with respect to the x-axis can help determine the size, shape and location of feet 26 and 36 with respect to bone contact surface 13 to help ensure the patient's posterior condylar prominences are properly referenced. Exemplary data points relating to posterior condylar prominences of a left, female femur bone are depicted in FIG. 2. Data point 56 relates to a lateral posterior condylar prominence and has an x and y value with respect to the origin. Data point 58 relates to a medial posterior condylar prominence and also has an x and y value with respect to the origin.

In the case of sizer 10 of FIGS. 1A and 1B, the population of femur bones extracted from the SOMA database is further refined to left leg, female femur bones. Data points having x and y coordinates corresponding to the location of the posterior condylar prominences is collected from each of these left leg, female femur bones and compiled into two datasets. The first dataset corresponding to the location of the posterior condylar prominence of the lateral condyle, and the second dataset corresponding to the location of the posterior condylar prominence of the medial condyle. The mean and standard deviations for each dataset are determined, which is then utilized to determine the area and shape of the reference surfaces of lateral and medial feet 26, 36 and the location and orientation of these surfaces with respect to bone contact surface 13.

The resultant shape of each reference surface 28, 38, which is derived from the standard deviation and mean, is an ellipse with the mean as the center or centroid 29, 39 (best shown in FIG. 4B) of the area defined by the ellipse and the standard deviation determining the major and minor axes of the ellipse. The resultant ellipse is preferably determined by the third standard deviation, which provides a 99.7% probability that the posterior condylar prominences of the left leg of a female patient will be tangentially contacted by the reference surfaces of each foot 20, 30 when bone contact surface 13 contacts a distal resected surface or unresected distal condyles. While the third standard deviation is preferred, the first, second or fourth standard deviation may be utilized. In one embodiment, the shape of reference surfaces 28 and 38 may be in the shape of a polygon or circle having a periphery that extends up to or beyond the third standard deviation from the centroid in all directions. In other words, reference surfaces 28 and 38 may have numerous shapes and sizes, but the standard deviational ellipse of the first and second dataset may set the minimum boundaries of such reference surfaces.

A trend of each data set may be generated to create a line slope that determines the orientation of the center line of each ellipse within the coordinate system. As best seen in FIG. 1B, the ellipses of each reference surface 28, 38 are generally oriented in an outwardly facing direction from each respective leg 20, 30.

In addition, the locations of the mean of each dataset, with respect to the x-axis can be utilized to determine the spacing of the reference surfaces in a proximal-distal direction from bone contact surface 13. As the fixed x-axis lies tangent to each distal condylar prominence of the population (or offset therefrom based on a relative location and orientation of a distal resected surface), the x-axis can be correlated to bone contact surface 13 of body 12, which, in use, would lie tangent to the distal condylar prominences (or distal resected surface) of the patient. Thus, the y-value of the mean with respect to the x-axis should substantially correspond to the proximal-distal distance between each centroid 29, 39 and bone contact surface 13. Additionally, in lieu of attempting to correlate the fixed origin 52 to bone contact surface 13, the locations of centroids 29, 39 in a lateral-medial direction may be determined with respect to each other. Thus, the difference of the x-values corresponding to each mean may be used to determine the lateral-medial distance between each centroid 29, 39, and thus the lateral-medial distance separating each foot 20, 30.

In some embodiments of A/P sizer 10, body 12 can be long and wide with a broad bone contact surface to help ensure that the distal condylar prominences are contacted by surface 13 while reference surfaces 28 and 38 simultaneously contact the posterior condylar prominences. In other embodiments, where a smaller profile body is desirable, such as when utilized in a minimally invasive TKA, datasets containing locational information of the distal condylar prominences may be utilized to help determine the size of body 12 and the location, in an anterior-posterior direction, of body 12 with respect to reference surfaces 28 and 38 to help ensure simultaneous contact with each prominence.

As such, the coordinate system utilized to determine the locations of each data point may be a three dimensional coordinate system, such as a three dimensional Cartesian coordinate system wherein each data point has an x, y, and z value as measured from a fixed origin. The x and y values may be utilized as previously described to determine the shape, orientation and location of reference surfaces 28 and 38 with respect to the bone contact surface. In addition, the z value of each data point may provide anterior-posterior location information of the posterior condylar prominences with respect to the distal condylar prominences to help determine the spacing between a posterior reference plane defined by reference surfaces 28 and 38 and body 12.

In one example, a fixed x-axis may lie tangent to the posterior condylar prominences of individual femur bones within a population with a fixed origin located at the lateral posterior condylar prominence. The anterior-posterior distance or z-values are determined by measuring from the x-axis to each distal condylar prominence of both the lateral and medial condyles of the population. A dataset of these measurements may be compiled within a refined population of left leg, female femur bones. The mean and standard deviation of this dataset may be determined, which may then be used to determine the outer boundaries of body 12 and spacing of these outer boundaries from the reference surfaces of feet 20 and 30.

In addition, as mentioned above, the lateral-medial L/M width of body 12 may be determined by compiling a dataset containing data points each corresponding to a distance separating lateral and medial distal condylar prominences within a particular predetermined population of femurs. In some embodiments, the predetermined population may be refined to be left leg female, right leg female, right leg male, or left leg male specific. The dataset may then be utilized to determine the minimum L/M width of body 12. In one example, the minimum L/M width of body 12 may be the sum of the mean distance and third standard deviation of the dataset. In another example, the minimum L/M width of body 12 may be the sum of the mean distance and the second or first standard deviation of the dataset. In a further example, the minimum distance may be the mean distance derived from the dataset.

A/P sizer 10 may be made from any biocompatible material including, but not limited to, titanium, cobalt-chromium, tantalum, niobium, stainless steel, polyethylene, and the like. Further, each A/P sizer 10 may be constructed from a single piece of raw material into a monolithic structure, or may be an integrated construction wherein body 12, each legs 20 and 30, and/or feet 26 and 36 are formed separately and then pieced together into a single, integrated structure. In other embodiments, A/P sizer 10 may be a modular construction in which body 12, legs 20 and 30, and/or feet 26 and 26 are formed separately and made connectable so that the operator can assemble A/P sizer 10 in the operating room during or just prior to the procedure. Such modularity may be beneficial where certain characteristics of the patient are best determined in the operating room. For example, a kit may be provided that includes a plurality of legs each having varying proximal-distal lengths designed to compensate for severe cartilage degeneration of the distal femur, which may be assessed during the procedure, so that the when the operator places contact surface 13 against the degenerated condylar surfaces, reference surfaces 28 and 38 will be properly located with respect to the posterior condylar prominences.

A/P sizer 10, may be utilized to perform various functions, such as sizing the final prosthesis, and setting the I/E rotation and A/P position of the final prosthesis. Sizing may be achieved by simultaneously contacting the distal condylar prominences (or planar distal resected surface) with bone contact surface 13, contacting the posterior condylar prominences with reference surfaces 28 and 38, and contacting the anterior cortex of the femur with a stylus, such as stylus 70 depicted in FIGS. 4A and 4B. The stylus can be engaged to sizer 10 via the engagement slot and may include indicia that indicate the femoral prosthesis size.

With bone contact surface 13 and reference surfaces 28 and 38 contacting the condylar prominences, the I/E rotation and A/P position of the final prosthesis can be set by drilling holes into the femur bone through the first and second apertures 14, 16. The holes may then be utilized by other surgical instruments, such as a 4-in-1 cutting block and by the final prosthesis.

In general, certain current A/P sizers are typically set up to orient an axis intersecting these holes three degrees in external rotation from the patient's posterior condylar axis. A common technique in performing a TKA is to resect the proximal tibia perpendicular or orthogonal to the tibial shaft axis. The posterior condyles are then resected along a plane parallel to the proximal tibial resection, which is presumed to be about 3 degrees externally rotated from the posterior condylar axis.

However, three degrees of external rotation is a broad presumption about the entire population of patients and is prone to inaccurate results when related to a specific patient. As such, the first and second apertures 14, 16 of sizer 10 may be oriented with respect to a posterior reference plane defined by reference surfaces 28 and 38 based on a dataset extracted from a population of angular relationships between tibia and femur bones in order to more accurately match the specific patient's anatomical condition.

Figure 3:
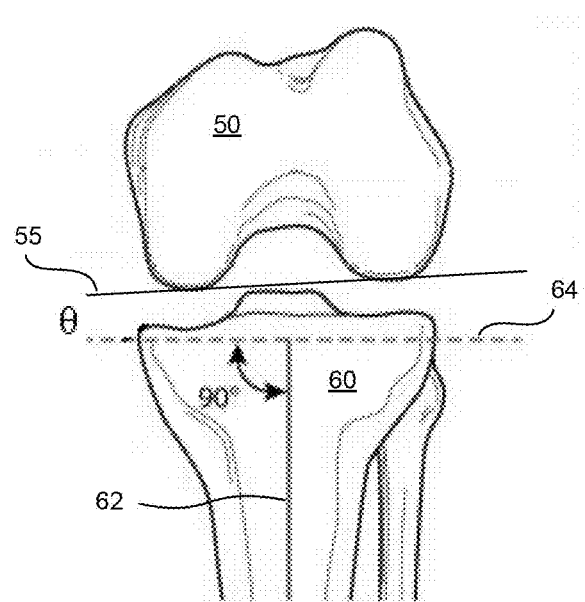
FIG. 3 is a schematic view of a femur and a tibia.

In one example, the population is refined to be left leg, female specific, and a dataset is compiled of data points where each data point corresponds to an angle $\theta$. As depicted in FIG. 3, angle $\theta$ is the angle between a transverse axis 64 defined by a proximal tibial resected surface, which is predetermined to be orthogonal to a tibial shaft axis 62, and a posterior condylar axis 55. The mean angle $\theta$ of the dataset may be utilized by A/P sizer 10 as the angle between axis 18, and thus apertures 14 and 16, with the posterior reference plane defined by reference surfaces 28 and 38. In some embodiments, a median angle $\theta$ may be determined from the dataset and utilized in lieu of the mean angle $\theta$.

Figure 1D:
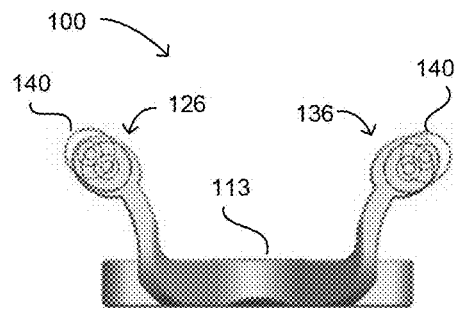
FIG. 1D is a bottom view of the A/P sizer of FIG. 1C.

FIGS. 1C and 1D depict one embodiment of a right leg, female specific A/P sizer. Sizer 100 is similar to sizer 10 in that sizer 100 includes a body 112, legs 120, 130, and feet 126, 136. Further, sizer 100 is similar in that body 112 includes apertures 114, 116 and an engagement slot 115 that opens in a medial to lateral direction. However, sizer 100 differs in that the area, orientation and location of the reference surfaces 128, 138 of feet 120 and 130 with respect to body 112, while determined in substantially the same way as with sizer 10, is based on a population of individual femur bones that is further refined to be right leg, female femur specific. Thus, while still generally an elliptical shape, the area, orientation and location of reference surfaces 128 and 138 are specific to that population.

In addition, the axis 118 intersecting first and second apertures 114, 116 is oriented oppositely to axis 18 to account for the desired external rotation of sizer 100 with respect to the right leg being opposite that of the left leg. Additionally, the angle between axis 118 and a posterior referencing plane defined by referencing surfaces 128 and 138 may differ from that of sizer 10 in that this angle may be specific to the selected population, which is determined in a similar fashion as previously described.

Figure 5A:
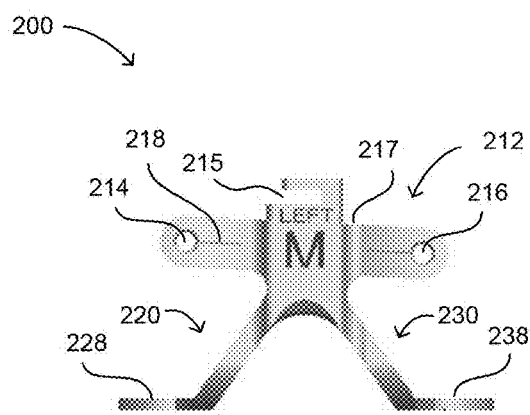
FIG. 5A is a front view of left leg, male specific A/P sizer.
Figure 5C:
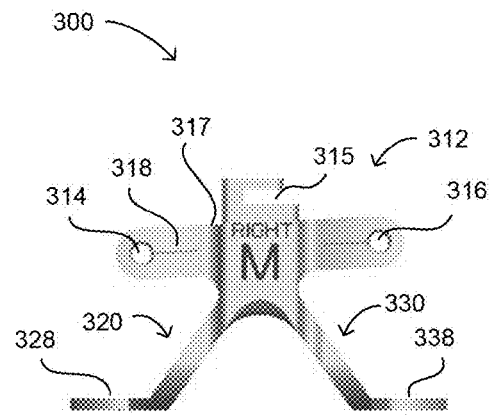
FIG. 5C is a front view of a right leg, male specific A/P sizer.
Figure 5B:
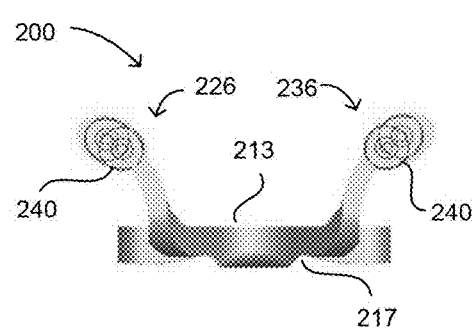
FIG. 5B is a bottom view of the A/P sizer of FIG. 5A.
Figure 5D:
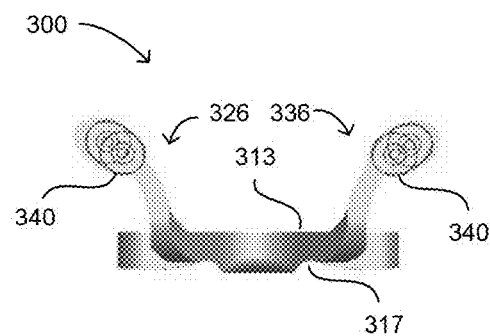
FIG. 5D is a bottom view of the A/P sizer of FIG. 5C.

FIGS. 5A and 5D depict one embodiment of a left leg, male specific A/P sizer 200. Sizer 200 is similar to sizer 10 in that sizer 200 includes a body 212, legs 220, 230, and feet 226, 236. Further, sizer 200 is similar in that body 212 includes apertures 214, 216 and an engagement slot 215 that opens in a medial to lateral direction. However, unlike sizer 10, body 212 includes anteriorly-posteriorly running grooves 317 that allow the operator to pinch and control body 212 opposite bone contact surface 213. Such features could also be included in sizers 10 and 100.

Further, sizer 200 differs from sizer 10 in that the area, orientation and location of the reference surfaces 228, 238 of feet 220 and 230 with respect to body 212, while determined in substantially the same way as with sizer 10, is based on a population of individual femur bones that is further refined to be left leg, male femur specific. Thus, while still generally an elliptical shape, the area, orientation and location of reference surfaces 228 and 230 are specific to that population. In addition, the axis 218 intersecting apertures 214 and 216 is oriented at an angle with respect to a posterior referencing plane specific to that population, which is determined in a similar fashion as previously described.

FIGS. 5C and 5D depict one embodiment of a right leg, male specific A/P sizer. Sizer 300 is similar to sizer 10 in that sizer 300 includes a body 312, legs 320, 330, and feet 326, 336. Further, sizer 300 is similar in that body 312 includes apertures 314 and 316 and an engagement slot 315 that opens in a medial to lateral direction. However, unlike sizer 10, body 312 includes anteriorly-posteriorly running grooves 317 that allow the operator pinch and control the body 312 opposite the bone contact surface 313.

Further, sizer 300 differs in that the area, orientation and location of the reference surfaces 328, 338 of feet 320 and 330 with respect to body 312, while determined in substantially the same way as with sizer 10, is based on a population of individual femur bones that is further refined to be right leg, male femur specific. Thus, while still generally an elliptical shape, the area, orientation and location of reference surfaces 328 and 338 are specific to that population.

In addition, the axis 318 intersecting first and second apertures 314, 316 is oriented oppositely to axis 18 to account for the desired external rotation of sizer 300 with respect to the right leg being opposite that of the left leg. Additionally, the angle between axis 318 and a posterior referencing plane defined by referencing surfaces 328 and 338 may differ from that of sizer 10 in that this angle may be specific to the selected population, which is determined in a similar fashion as previously described.

In an effort to provide contrast between resultant contact surfaces of various populations, FIGS. 1B, 1D, 5B, and 5D each depict an overlay of reference surfaces of different but related populations. For instance, FIG. 1B depicts an overlay 40 of resultant reference surfaces of a left leg, male specific population, and FIG. 1D depicts an overlay 140 of resultant references surfaces of a right leg, male specific population. In addition, FIG. 5B depicts an overlay 240 of resultant reference surfaces of a left leg, female specific population, and FIG. 5D depicts an overlay 340 of resultant references surfaces of a right leg, female specific population. Thus, as shown, a variety of population inputs can be utilized to accurately accommodate a particular patient.

While the embodiments above include a planar reference surface 13, 113, 213, and 313 for contacting unresected distal condyles or a planar distal surface, other embodiments are contemplated having a body suited specifically for contacting unresected distal condyles. For example, body 12 of sizer 10 may have hands each with their own reference surface in lieu of single contact surface 13. Such hands may be connected by arms extending from legs 22 and 32 and may be similar to feet 26 and 36, but specifically configured based on the relative locations of distal condylar prominences 51 and 52, as described above. Thus, in such an embodiment, the sizer would have two feet for simultaneously referencing lateral and medial posterior condylar prominences of a femur and two hands for simultaneously referencing lateral and medial distal condylar prominences of the femur.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of manufacture of a surgical reference guide, comprising the steps of:
   forming a body having a contact surface;
   extracting a dataset from a database, the dataset comprised of a plurality of data points each corresponding to an individual bone within a population of bones and each corresponding to a location of a preselected point on the bone within a predetermined coordinate system; and
   forming a foot having a first reference surface having an area defined by a standard deviation of the dataset, and said foot connected to the body via a leg.

2. A method of manufacture of a reference foot of a surgical reference guide having a body and at least one leg extending from the body, comprising the steps of:
   selecting a dataset from a database, the dataset comprised of a plurality of data points each corresponding to a location of a point on an individual bone within a population of bones and within a predetermined coordinate system;
   determining a mean and standard deviation of the dataset; and
   forming a reference surface of the reference foot such that the reference surface has an area based on a standard deviation of the dataset.

3. The method of claim 2, wherein determining the standard deviation includes determining the third standard deviation of the dataset.

4. The method of claim 3, wherein the area includes a centroid and an outer boundary, the outer boundary being spaced from the centroid a distance substantially equal to the third standard deviation of the first dataset.

5. The method of claim 4, further comprising:
   determining a line slope of the dataset; and
   coupling the reference foot to the at least one leg such that the reference foot has an orientation with respect to a contact surface of the body based on the line slope.

6. A method of manufacture of a surgical reference guide, comprising the steps of:
   determining a mean distance of a posterior condylar prominence from a distal condylar prominence from a population of femurs;
   forming a body having a planar contact surface;
   forming a leg extending from the body; and
   forming a foot extending from the leg and being spaced from the reference surface based on the mean distance.

7. The method of claim 6, wherein forming the foot includes forming a reference surface disposed on the foot having an area, the area having a centroid spaced from the reference surface a distance substantially equal to the mean distance.

8. The method of claim 7, wherein the area is defined by a standard deviation from a mean location within a preselected coordinate system of the posterior condylar prominence within the population of femurs.

\* \* \* \* \*